(12) United States Patent
Cirri et al.

(10) Patent No.: US 8,790,589 B2
(45) Date of Patent: Jul. 29, 2014

(54) STERILIZATION SYSTEM FOR PET CONTAINERS AND BOTTLES

(75) Inventors: Gianfranco Cirri, Sesto Fiorentino (IT); Maria Prudenziati, Modena (IT)

(73) Assignee: S.I.P.A. Societa Industrializzazione Progettazione E Automazione S.p.A., Vittorio Veneto (IT)

( * ) Notice: Subject to any disclaimer, the term of this patent is extended or adjusted under 35 U.S.C. 154(b) by 1075 days.

(21) Appl. No.: 12/596,003

(22) PCT Filed: Apr. 18, 2008

(86) PCT No.: PCT/IB2008/000946
§ 371 (c)(1),
(2), (4) Date: Apr. 6, 2010

(87) PCT Pub. No.: WO2008/129397
PCT Pub. Date: Oct. 30, 2008

(65) Prior Publication Data
US 2010/0209290 A1     Aug. 19, 2010

(30) Foreign Application Priority Data

Apr. 18, 2007 (IT) .............................. MO2007A0137

(51) Int. Cl.
*A61L 2/08* (2006.01)
(52) U.S. Cl.
USPC ...................... 422/292; 250/492.1; 250/492.3
(58) Field of Classification Search
USPC ....................... 422/22, 292; 250/492.1, 492.3
See application file for complete search history.

(56) References Cited

U.S. PATENT DOCUMENTS

| 3,780,308 | A | 12/1973 | Nablo |
| 6,617,596 | B1 * | 9/2003 | Korenev ..................... 250/492.3 |
| 7,067,827 | B2 * | 6/2006 | Bol et al. ................... 250/492.2 |
| 7,759,661 | B2 * | 7/2010 | Avnery ....................... 250/493.1 |
| 7,767,987 | B2 * | 8/2010 | Eguchi et al. .............. 250/492.3 |
| 2002/0114728 | A1 | 8/2002 | Kulish et al. |

FOREIGN PATENT DOCUMENTS

| CN | 1638813 A | 7/2005 |
| EP | WO2005/002973 A1 | 1/2005 |
| FR | 2 815 542 A1 | 10/2000 |
| JP | 2005 247427 | 9/2005 |
| WO | WO 03/075964 | 9/2003 |

OTHER PUBLICATIONS

JP04 132555 partial EngTranslation, May 6, 1992, Sumitomo Heavy Ind.
JP11 248896 partial EngTranslation, Sep. 17, 1999, Mitsubishi Heavy Ind.
JP2000214300 partial EngTranslation, Aug. 4, 2000, Mitsubishi Heavy Ind.
JP200776704 partial EngTranslation, Mar. 29, 2007, Mitsubishi Heavy Ind.
JP 2005 247427 English Machine Translation and bibliographic data, Sep. 15, 2005, Mitsubishi Heavy Ind.

* cited by examiner

*Primary Examiner* — Sean E Conley
(74) *Attorney, Agent, or Firm* — Sampson & Associates, P.C.

(57) ABSTRACT

A sterilization system for PET containers and bottles including at least one electron flow generator 1, a scan gun 2 and at least one target 4 preferably made of heavy metal, so that when a part of the electron radiation hits said target a reflected X ray radiation is generated, which contributes to the sterilization of the containers. A certain amount of liquid or gaseous oxygen which upon collision with the electron radiation is converted to ozone is also exposed to the radiation, thus further contributing to the sterilization.

13 Claims, 9 Drawing Sheets

STERILIZATION SYSTEM FOR PET CONTAINERS AND BOTTLES

FIELD OF THE INVENTION

The present invention relates to the sterilization of item surfaces and gases and specifically to the sterilization obtained mainly by means of the interaction of electrons with item surfaces and environments and with gas or air contained or flowing therein and to synergistic effects thereof.

STATE OF THE ART

In the fields of medicine, pharmaceutical production and food processing, the need for sterilization is critical for the protection against the risk deriving from detrimental microorganisms. Most of the sterilization methods used nowadays require that the sterilizing agent systematically penetrates the item to be sterilized. These methods include the sterilization by means of heat, where the item to be sterilized is subjected to heating and pressure, for instance in an autoclave. Heat and pressure penetrate within the item to be sterilized and kill the detrimental microorganisms after a sufficient time. Gases such as hydrogen peroxide or ethylene oxide are also used to sterilize items. The gas needs to permeate the entire item for a complete sterilization. An alternative sterilization method employs ionizing radiations, such as gamma rays, X rays or high energy electrons.

There are however many target items in which the exposure to sterilizing agents would cause deleterious effects for the item itself. Examples include items which would melt or would deteriorate upon exposure to heat, products which would deteriorate or react with the sterilizing chemical agents, and materials which would detrimentally be altered upon exposure to high energy radiation, especially ionizing radiations. It has been recognised in the past that the deleterious effect does not occur if the ionizing radiation remains confined to the surface of the target item. However, most of the ionizing radiations are generated by powerful beam generators, such as accelerators, so that the resulting radiation beam is by its own nature penetrating.

U.S. Pat. No. 4,801,427 discloses a process for the dry sterilization of medical equipment subjected to an electric discharge in a gaseous atmosphere, which produces an active plasma. In an embodiment, Jacob discloses how items are placed on a conveyor belt which leads them to a gap where an atmospheric-pressure discharge is generated by corona discharge in ambient air. The plasma is formed by discharge between the conveyor belt, which is grounded and acts as a cathode, and a plurality of needle-shaped nozzles, which act as anodes, which disperse a ionizing gas; such a gas may be an oxidizing gas such as oxygen, or a reducing gas, such as hydrogen.

U.S. Pat. No. 5,200,158 discloses the sterilization by exposure of an item to a gas plasma generated by an electric discharge in a gaseous atmosphere under reduced pressure. Hydrogen, oxygen, nitrogen and inert gases are all recommended as possible gases for the formation of the plasma.

As opposed to the high energy approach of this patent, U.S. Pat. No. 3,780,308 to S. Nablo discloses the sterilization of item surfaces by using low-energy electrons, although there is a particularly high energy starting point. One of the advantages of low-energy electrons is that, as they do not penetrate in the volume of the item, they do not modify the mechanical properties of the material to be sterilized. Nablo has broadened his idea with U.S. Pat. No. 4,652,763, which discloses the use of an electron beam having an energy sufficient to penetrate the outer layer but not such as to pass through the inner layer of the target material.

Several patents disclose the use of a gas plasma to obtain the surface sterilization. In U.S. Pat. No. 3,948,601, Fraser et al. disclose the use of a continuous flow gas plasma, introduced at a very low pressure in a chamber containing the target item to be sterilized. A cold plasma is continuously produced by a gas such as argon, by means of the exposure to a radiofrequency field. One of the problems encountered in the previously devised devices is connected to three-dimensional structures, such as vials, cuvettes and sleeves. Sometimes these structures have profiles which generate shadow areas for a ionizing radiation beam and not even a diffused discharge such as electrons or reactive ions reaches such areas which will result poorly sterilized. A solution would be to rotate or direct the item to be sterilized at a different angle.

Another possibility claimed in U.S. Pat. No. 6,623,706B2 consists in using two electron generators positioned one in front of the other with respect to the item to be treated, so as to each cover the shadow areas left by the other.

Recently there have been many publications and patents related to sterilization methods, such as U.S. Pat. No. 6,682,696 B1, 2004, related to the use of hydrogen peroxide, US Patent No. 2004/022673 which provides for the use of peracetic acid, formalin, etc, U.S. Pat. No. 6,945,013, which employs hydrogen peroxide and ozone. U.S. Patent No. 2006/0032189 as well as U.S. Patent No. 2007/0065335 and U.S. Pat. No. 6,432,279, 2002, provide for ozone and water-dissolved ozone.

Therefore, the main technical problem to be solved is to achieve the sterilization of elaborate-shaped containers without subjecting them to deteriorating temperatures for the container itself, such as PET containers.

SUMMARY OF THE INVENTION

It is the object of the present invention to provide a sterilization, sealing and marking system for PET containers and bottles adapted to solve the above said problems. The solution is carried out by means of a sterilization system for PET containers and bottles, according to claim 1.

According to another aspect of the invention, said problems are solved by means of a sterilization method according to claim 12.

The dependent claims disclose preferred embodiments of the invention, thus forming an integral part of the present description.

BRIEF DESCRIPTION OF THE DRAWINGS

Further features and advantages of the invention will become more apparent in light of the detailed description of a preferred though not exclusive embodiment of a sterilization, sealing and marking system for PET containers and bottles, shown by way of non-limitative examples, with the aid of the accompanying drawings in which.

Similar reference numbers and letters in the figures identify similar elements or components.

DETAILED DESCRIPTION OF PREFERRED EMBODIMENTS OF THE INVENTION

The innovative, flexible and totally computerized system includes one or more generators 1 of electrons with a low-voltage, approximately on the order of 200-400 KeVs and magnetic field generators or deflectors 3 and programmable post-acceleration sections for the electron beam, which allow to make the best of the peculiarities of an electron beam both in the field of sterilization and in the field of polymerization, both for the sealing of the surface of the bottles and for their marking and also for their aseptic filling.

The present invention makes the best of the synergies of all of the specifications and various peculiarities of electron beams in the new moulding, sterilization and filling systems for PET containers: sterilization, ozone production, plasma, polymerization, heating and production of X rays, etc. aided by the introduction of the new heating method based on Atmospheric Plasma Spray (APS) technology, providing:
1. optimization of the dose uniformity;
2. use of PC-programmable sources of electrons on the order of 200-400 KeVs, including at least one scanning horn or gun 2 and with a window 21 with the beam entering at a 90° angle;
3. use of PC-programmable magnetic fields 31 for the deflection of scattered electrons;
4. use of PC-programmable electronic post-acceleration fields incident on sectors for the generation of X rays;
5. flexible and PC-programmable raster or orientation of the beam scan;
6. sterilization of equipment, environment and containers with $O_3$ generated by the electron beam and by UV;
7. polymerization of sealing paint with an electronic beam;
8. polymerization of date stamp, mark, etc. by an electron beam;
9. heating with APS technology.

Therefore, the object of the present invention is an integrated, flexible and computerized system for the sterilization in general and for PET preforms, bottles and containers for food in particular, which employs the ionizing radiation without negatively affecting the PET substrate. One of the main objects is in fact to obtain an aseptic container by effect both of the direct radiation and by all of the other devices which will be disclosed, thus optimizing the uniformity of the dose released in the container. This integrated and flexible system is more efficient and cost-effective than previously devised sterilization devices, as it combines the direct effect of the low-energy electrons of the beam with the synergistic effect of X rays, ozone and plasma generated by the electron beam itself, and uses the introduction of the heating processes and APS technology.

The invention achieves the object of an effective sterilization without needing to resort to high energies with expensive and voluminous equipment and without requiring an excessively high and expensive power, equipment which is moreover subject to especially restrictive and elaborate health and licensing standards, but instead simply employing the synergy of the electron beam with the effects associated thereto: plasma, ozone, X rays, sterilization and polymerization.

Figure 1:
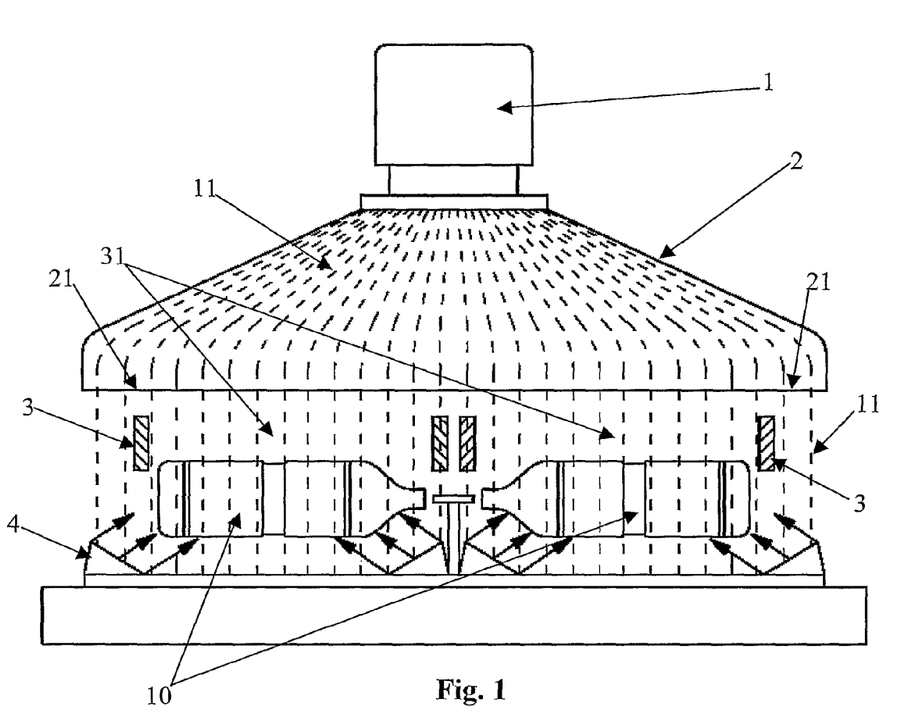
FIG. 1 shows a cable-and-trunk schematic of sterilization for containers by means of radiations.
Figure 2:
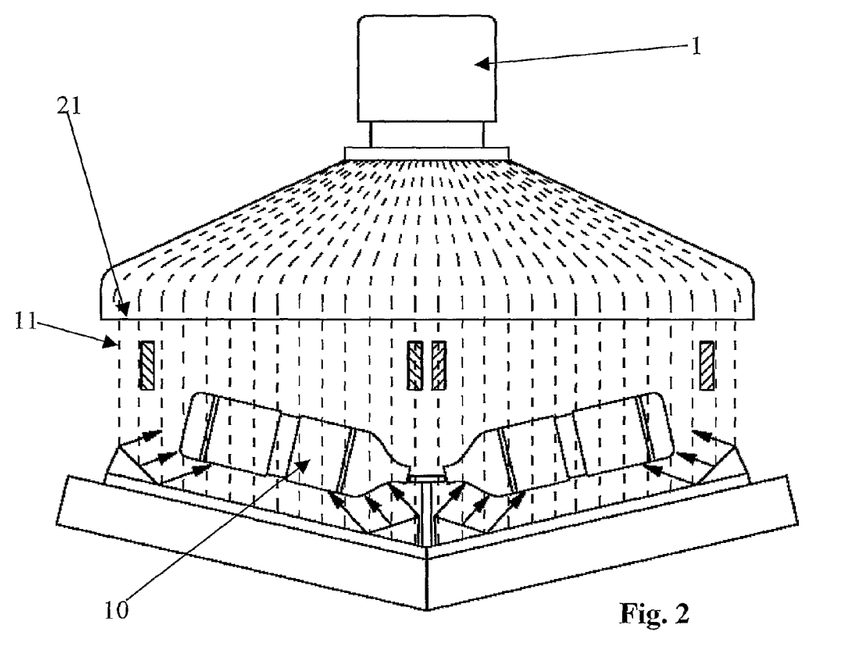
FIG. 2 shows a configuration similar to the previous figure, in which the containers to be sterilized are arranged at a different radiation exposure angle.
Figure 3:
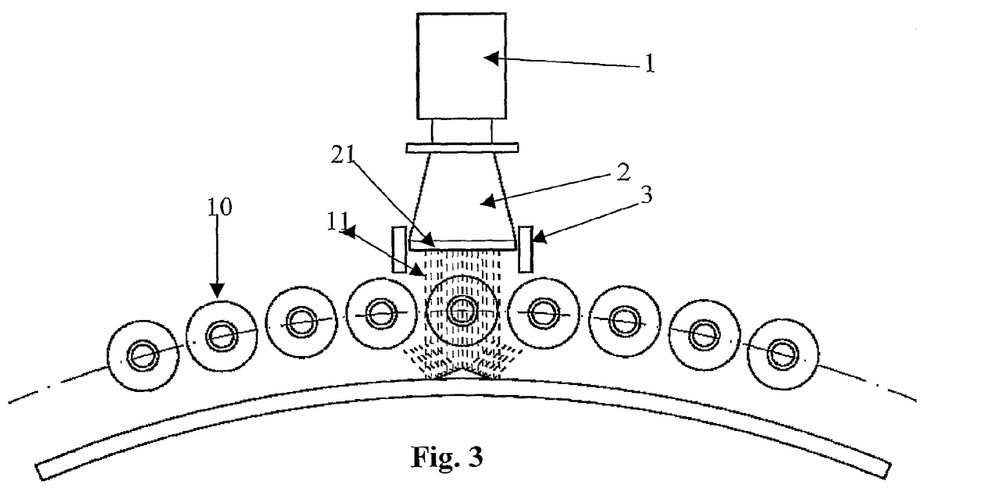
FIG. 3 shows a cable-and-trunk schematic in which the containers to be sterilized move along a circumference and are exposed to the radiations one at a time.
Figure 4:
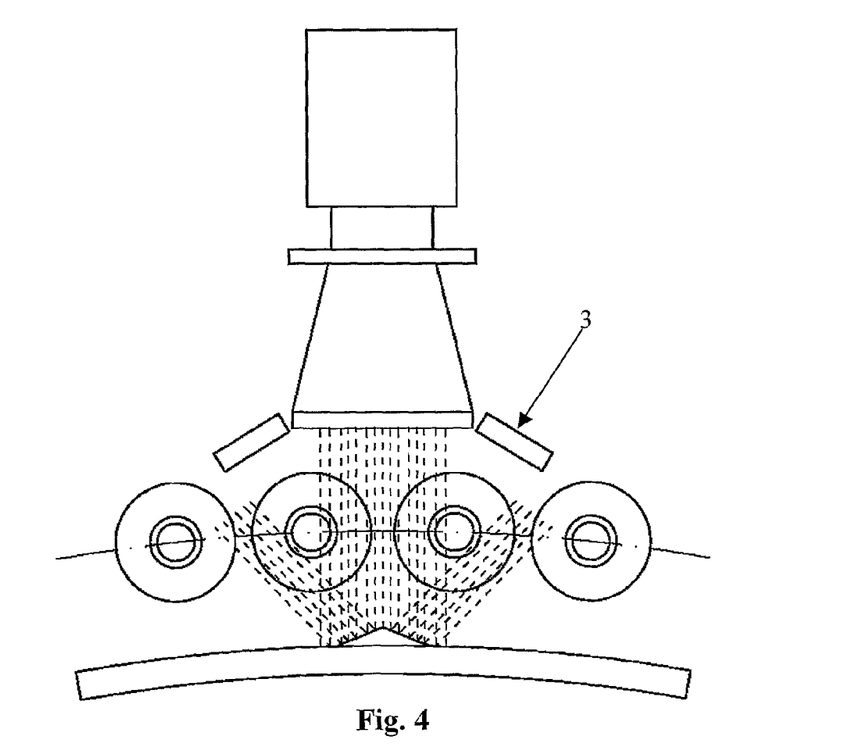
FIG. 4 shows, with respect to the previous figure, a different configuration of the irradiation of the containers.
Figure 5:
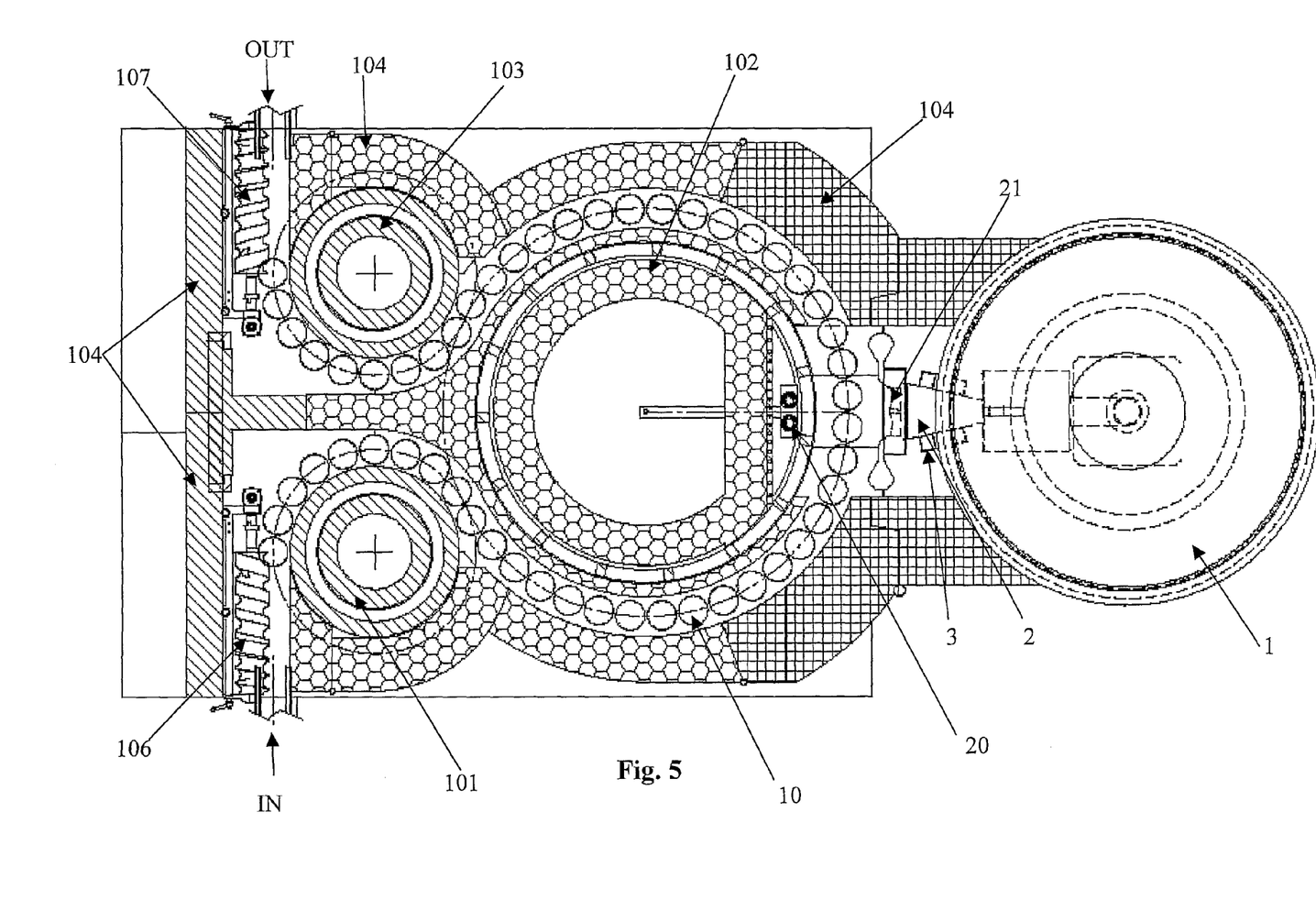
FIG. 5 shows a section view of a sterilization system highlighting the wheeled handling system and the electronic flow generator.
Figure 6:
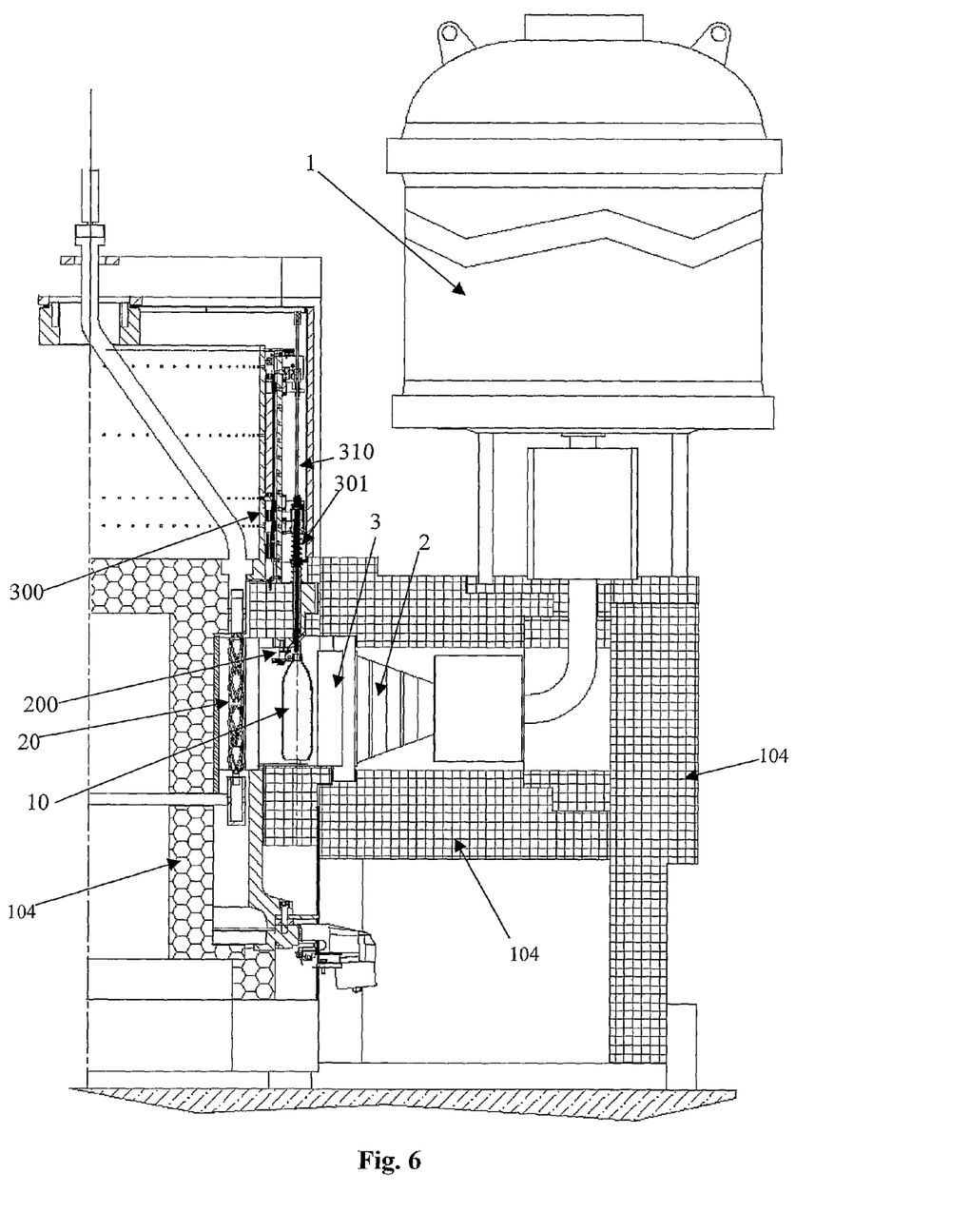
FIG. 6 shows a portion of a vertical section corresponding to the previous figure, highlighting the irradiation area of the containers and of corresponding capsules, the generator and the corresponding electron accelerator.
Figure 7:
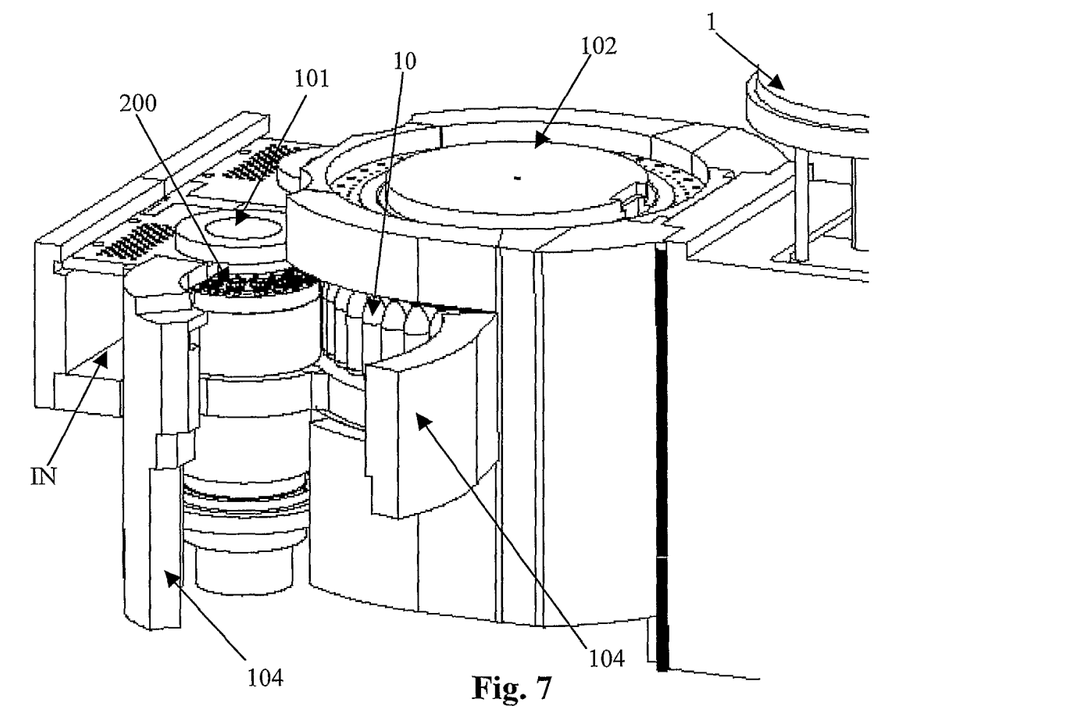
FIG. 7 shows a three-dimensional view of the system with open screening parts which allow a partial view of the handling system for the containers near the loading area.
Figure 8:
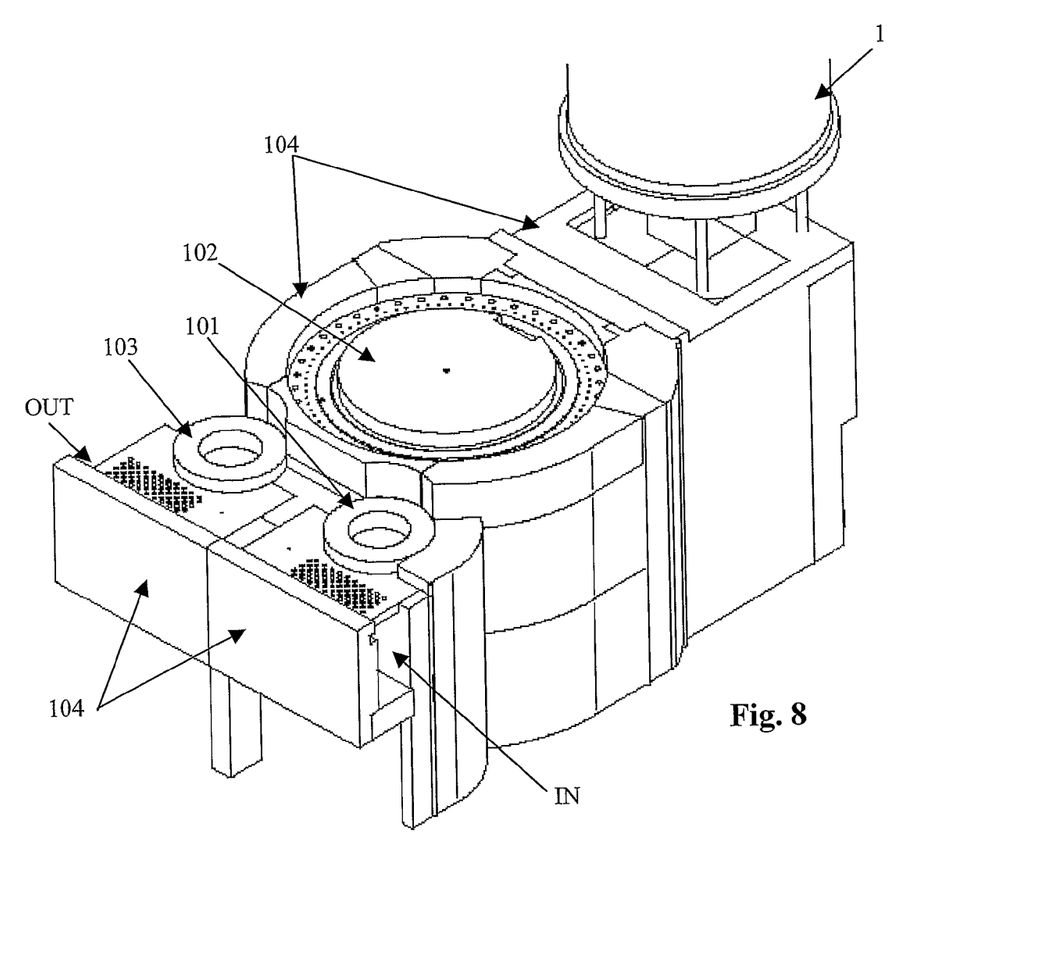
FIG. 8 shows another three-dimensional view of the system, by which view the position of the sterilization wheel, of the inlet wheel and of the output wheel for the containers may be deduced, all three forming the handling system.

Such a synergy is obtained by appropriate and specific devices such as:
1) the use of a compact outlet window 21 for the electrons for the use of appropriate magnetic fields 31, although the window extends, for example, in a vertical direction, to allow the direct and simultaneous irradiation of at least two bottles even having a different shape and size, thus allowing to achieve at least two transits under the beam for each single bottle, arranged according to the most appropriate orientation so as to have the best dose uniformity (FIGS. 1 and 2);
2) a better dose uniformity is also achieved in virtue of the use, FIGS. 3 and 4, of appropriately positioned PC-programmable magnetic fields 31, which direct the scattering of electrons outputted from the thin titanium window 21, with an opening preferably on the order of 0.15-0.05 μm, towards the shadow areas of the bottle, neck and bottom;
3) further advantages for the dose uniformity are achieved, as well as for the appropriate angle, see FIGS. 1 and 2, of the bottle with respect to the beam 11, by the rotation given to the bottle, for instance around its own symmetry axis, and made more effective by two transits under the beam;
4) another crucial contribution to the dose uniformity comes from the PC-programming of the scan raster, thus achieving the appropriate dose in the appropriate places;
5) a further contribution to the sterilization process is brought by the arrangement in appropriate spots of targets or reflectors 4 made of a heavy metal, such as W, Ta, Hf, etc. polarized so as to convey and make the sterilizing effect of the scattered electrons more effective by the simultaneous production of X rays;
6) finally, the introduction of a drop of liquid oxygen within the bottle gives rise to a more effective production of ozone, under the impact of electrons, with a strong contribution to the sterilization of the inner surface of the container.

To further optimize the synergies offered by the use of electric guns, the system further provides:
7) a position along the path of the bottles, where these are covered with a microporosity sealing paint, a paint which may be polymerized by electrons and which will therefore be polymerized when it passes under the beam;
8) similarly, along the path of the bottles, a position is provided, in which specific marks, date, etc. are applied with inks which polymerize by electron beams.

The invention also provides a further extension of the synergies offered by the use of electronic beams to also obtain the sterilization of the entire production and/or treatment system of preforms and/or bottles, thus handling and appropriately directing during this preliminary step the generator of electrons towards the various sectors of the system, so as to obtain the desired sterilization through the adjustment of the energy of the beam, the use of adjustable magnetic fields, of appropriately arranged and polarized heavy metal targets and of liquid oxygen drops.

This e-beam technology for the sterilization is aided in this flexible system by the introduction of the new heating technology based on the provision of ohmic resistive elements directly on the element to be heated, by the use of APS technology.

This new APS technique is used on this innovative system anytime it is economically convenient for the heating of equipment and components both to sterilize, and to fluidize plastic materials for the production of preforms for bottles etc. The diagram of how this technique is performed is shown in FIGS. 1 to 4. According to FIG. 1, the generator 1 of the electron beam 11 irradiates through the horn 2 a pair of bottles or containers to be sterilized 10. The electron beam 11 is appropriately directed by means of magnetic fields 31 generated by the magnetic field generators 3 so as to be focused on all of the areas of the bottle while the latter is caused to rotate around its own symmetry axis. Also shown are said polarized targets 4, which are adapted to deviate said electron flow 11 towards the areas of the bottle which are more critical for the process of sterilization.

With respect to FIG. 1, FIG. 2 suggests a different angle for the bottles 10 with respect to the direction of the electron flow 11.

FIG. 3 shows an example in which the bottles 10 are directed at different angles with respect to the previous figures in relation to the irradiated electron flow 11. At least one bottle 10 is directly irradiated by the electron beam, possibly directed by said magnetic field generators 3, while other bottles are hit by the radiation upon its reflection by said targets or reflectors 4, which may also be appropriately polarized.

FIG. 4 shows a different configuration of the magnetic field generators 3 while, with respect to FIG. 3, two bottles 10 are hit by the direct radiation and other two are hit by the reflected radiation.

According to a preferred embodiment of a sterilization system, shown in FIGS. 5 to 12, it includes a sterilization wheel 102 to which the bottles 10 are attached along its circumference by appropriate clamps 200 and carried in front of the mouth of the gun 2 which irradiates an electron flow.

Said sterilization wheel 102 is preferably coupled to an inlet wheel 101 and to an outlet wheel 103.

The entire path covered around said wheels is enclosed within a screening shell. Such a choice results from the need to screen the environment surrounding the system from the emissions of the generator 1, which are potentially harmful for human health.

Near the inlet indicated by "IN" and the outlet from the system indicated by "OUT" of the bottles 10, there are respectively worm screws 106 and 107, which serve the purpose of at first spacing and then drawing the bottles near, so that they are correctly spaced when the clamps 200 need to grip them by the neck and handle them in the path within the system.

Said worm screws 106 and 107 rotate synchronously to the handling system including said wheels 101, 102 and 103.

The configuration and the dimensional ratio between said wheels may be designed so as to maximize the labyrinth effect suitable for screening the system from outside.

The IN loading area and the OUT unloading area are the interface towards the external environment and must therefore form a barrier against the introduction of potentially polluted air within the sterilization system, accordingly an overpressure is generated therein with a complete filtration of the incoming air so as to maintain a class 100.

The transport of bottles to the IN inlet of the sterilization system, but also externally thereto, is preferably obtained by means of said synchronous worm screws or by a conveyor belt, in order to limit the introduction of potentially polluted air in the system.

The sterilization is carried out by means of the irradiation of an electronic beam produced by a generator 1 integrated by an accelerator machine.

The area near the irradiation horn 2 of the bottles is also maintained overpressurized with a laminar flow of air filtered by absolute filters, preferably class 100 filters, although with a lower overpressure than the IN loading area and OUT unloading area. The reason is the need to achieve an evacuation of the ozone produced by the electronic beam which has a strongly ionizing power, thus avoiding it from escaping in the environment surrounding the sterilization system. A handling of the containers to be sterilized, which allows the certain rotation of the same in front of the beam for at least two complete rotations, is preferably obtained.

As will be more apparent later, said handling is achieved so as not to screen any area of the container from the radiation, as the non perfect irradiation of all of the spots on the surface of the container to be sterilized would compromise the result of the sterilization. The width of the beam determines the irradiation time and the latter must in any case be appropriate for the safety of the mechanical handling system. Considering that for a safe and complete rotation the rotation speed may not be higher than 10 rounds/sec, i.e. 600 rounds/min, the exposure time results being about 0.1 seconds for a complete irradiation. The width of the beam is therefore proportional to the production throughput and to the pitch in the handling star. In the preferred embodiment, for a 112.5 mm spacing between the bottles, the width of the beam at bottle level needs to be at least two times said spacing, thus resulting 250 mm. The length of the beam is instead equivalent to the maximum length of the container plus an amount for the compensation of the edge effect.

For example, for a 350 mm long container, the length of the horn will be at least 400 mm.

The accelerator is positioned in a chamber adjacent to the irradiation area so as to limit the volume of the controlled environment. The gun installation chamber is in any case conditioned and over-pressurized and has features similar to the IN loading area.

A proportioned cooling system is provided preventing the incident power on the carrier system from bringing the areas in contact with the plastic of the container to a temperature above 60° C. The screening in the irradiation area also needs to be conditioned through the use of channelling in which a refrigerant fluid is run, for instance low temperature water.

The screening system 104 serves to reduce the emitted radiation, i.e. X rays, from the system to an acceptable range for the workers operating near the system. Indeed, the dangerousness is not related to the radiation of the electron beam generated by the generator 1, which is a beta radiation that is absorbed in a few tenths of a mm by a substance having a density equivalent to water, but instead to the transformation by collision with high molecular weight metals of the energy of the X ray beam. Materials, which strongly absorb X rays and have labyrinth geometries for open systems, such as the system object of the present invention, were therefore required.

As the use of lead as an absorbing material is a widespread practice for limiting the thickness of the wall, although this material should be avoided in a machine that processes containers for food products, as an alternative to lead, the screening shell 104 was then preferredly made of steel with a thickness proportionally greater than that which would have been required with lead, because of the lower density of steel which exerts a less effective screening effect for the X rays. The screening depends on the energy, on the photon flow generated by effect of the collision of electrons with the atoms of the screening material, on the materials used for the screening, on the amount of flow of radiation acceptable for the worker operating on the machine. In the case of a 1 MeV energy the thickness of the lead wall may be estimated to be equivalent to 350 mm; in the case of open systems such as the case of the system for bottles, the radiation must be reflected at least three times before reaching the outlet, as each reflection cuts 99% of the energy of the radiation.

This explains the special geometry of the sterilization system which includes said handling system, for instance by means of stars, including said wheels 101, 102 and 103 cooperating so as to lead the handling path to be similar to a Ω in a plan view.

The gripping device securing a bottle to said wheels during the handling of the bottle is a clamp 200 positioned on said stars.

The reflectors 4, such as the reflector 204 positioned above said gripping device (see FIG. 10) are positioned in the irradiation chamber and have a high atomic weight in order to promote the generation of X rays, thus contributing by at least 1% to the total production and, as mentioned above, contribute to the sterilization of the container.

The window 21 of the scan horn 2 includes at least one titanium sheet, which tends to heat during operation, therefore its cooling and the cooling of the generator 1 and of the scan horn 21 in general occurs by means of one or more jets of blown air, which is continuously recovered from the irradiation chamber and cooled by a heat exchanger or taken from outside and appropriately filtered.

In an advantageous variant of the invention, the sterilization of the capsules and caps 20 also takes place in the irradiation chamber. Placing them behind the containers targeted by the radiation, the residual electron radiation passing through the containers and that between adjacent containers are exploited by means of a controlled motion by a second appropriate belt or star spacing and handling system. Said second handling system carries the sterilized capsules from the irradiation chamber to the capping machine.

As an alternative, the handling of the capsules may provide a transit in an area adjacent to the heavy metal reflectors 4, to benefit from the X rays resulting indirect with respect to the direct electron radiation. When the capsules are exposed to direct and particularly intense and penetrating X rays, even the most elaborate capsules, such as the so-called "sport caps", may be sterilized.

The dose to be preferably achieved is always higher or equivalent to 10 kGy and, considering the transformation factor from electron flow to X ray flow of about 1%, the preferred exposure time for the capsule is about 100 times that of the container, i.e. 10 seconds.

In a preferred embodiment of said sterilization system, as the duration of the exposure corresponds to the axis of the emission horn, then the second handling system includes a feed screw within the screening wall with a determined path in order to ensure the above said preferred time of exposure. The capsules sterilized in this manner are then carried to a use station, for instance to the capping machine within the aseptic block.

The advantage of the irradiation by X rays instead of a direct electron beam also resides in the fact that often the capsules are made in polypropylene (PP) and this material is easily deteriorated if subjected to excess dosage of electron beam, whereas with X rays the radiation is considerably less powerful and more easily managed.

Sterile air or nitrogen, or another gas is considered to be required in the container during sterilization of the container itself in order to achieve two purposes: 1) the washing of the container from the presence of internal foreign bodies, before irradiating;
2) the washing of the container from the presence of ozone which is formed by the action of ionizing radiations during the process of sterilization.

Specifically, when an inert gas is introduced, the oxidation by ozone, generated by the electron flow, of the product which is later introduced in the container and is generally but not exclusively food, is avoided.

A washing air or gas inlet nozzle adapted to be introduced automatically in the container along the sterilization path and to nearly come into contact with the bottom is provided in order to achieve a good washing effectiveness.

As noted above, since it is most important to avoid screening areas for the radiations on the container, a special clamp 200 has been provided.

Figure 9:
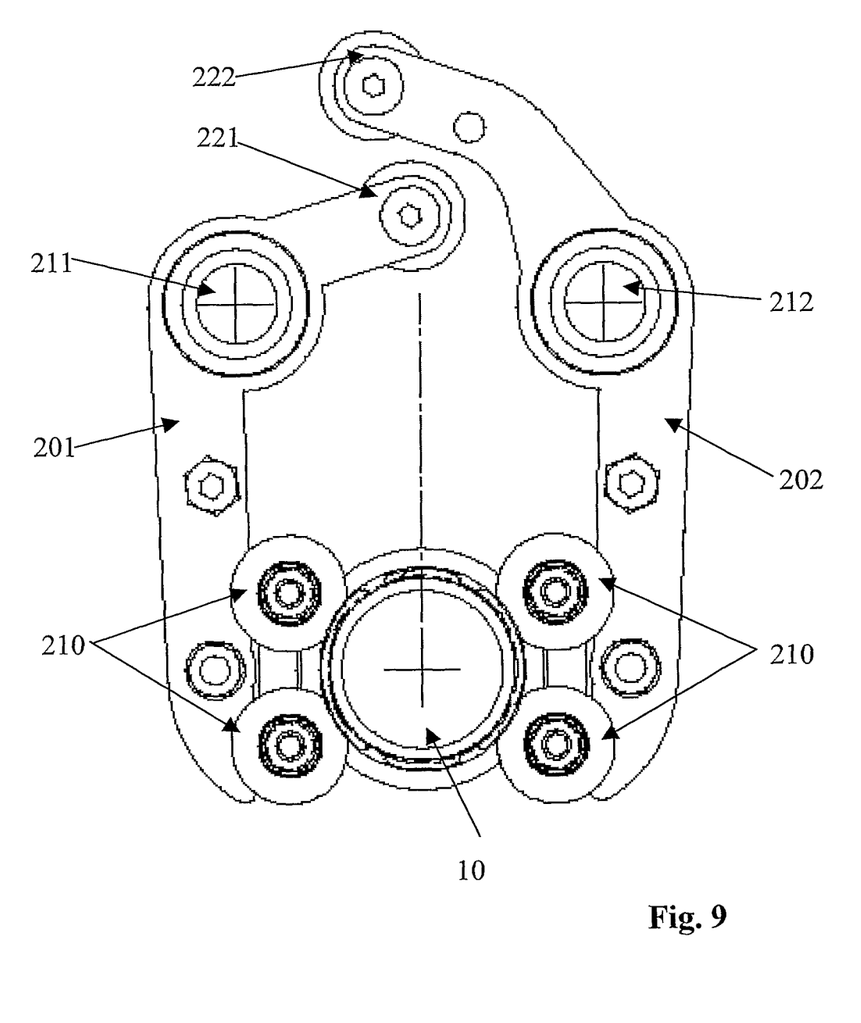
FIG. 9 shows a plan view of a clamp to grip a bottle to be sterilized.
Figure 10:
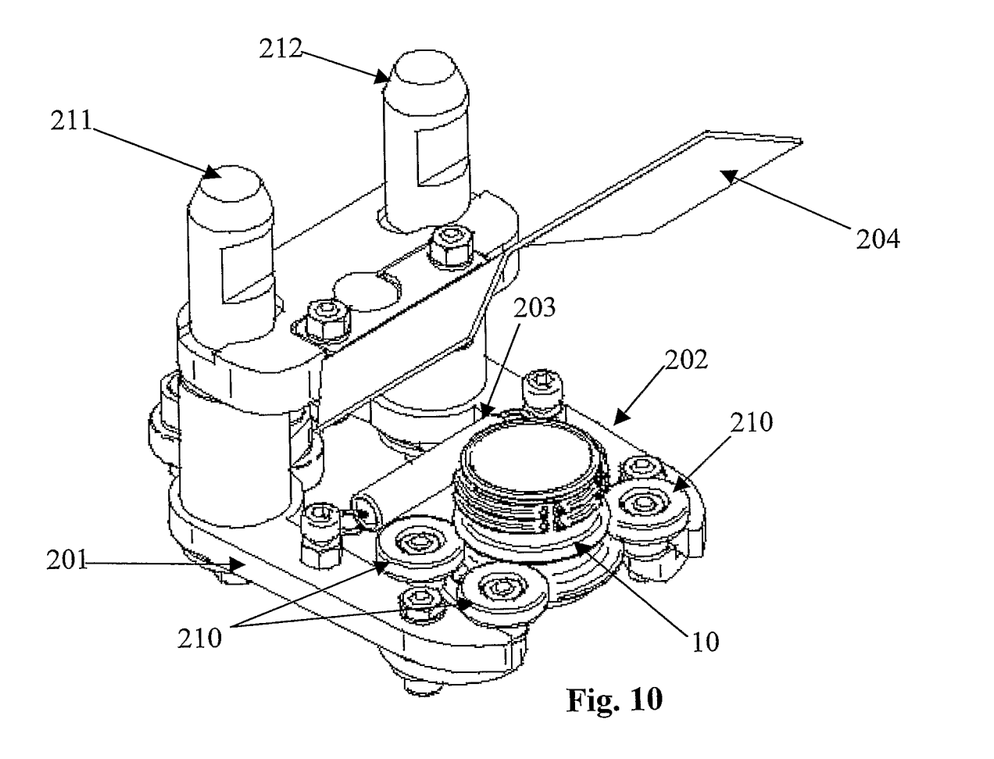
FIG. 10 shows a cavalier drawing view of the clamp of the previous figure.

Said clamp includes two elongated elements 201 and 202 which opposedly cooperate to grip the neck of a bottle. The grip is adjusted by the load of a spring 203 which tends to draw said opposed elements nearer. In the embodiment of FIGS. 9 and 10, each of these rotates about its own fulcrum, respectively 211 and 212. Furthermore, said elements which are elongated at one end, include gripping means 210 for the bottle neck, while at the other end they include control means 221 and 222 for opening the clamp 200.

Specifically, said gripping means 210 include a plurality of rollers distributed on both of the elongated elements to be adapted to the bottle neck to be gripped, leaving front and rear portions free, so that no area of the bottle is screened from radiations.

Said control means 221 and 222 for opening the clamp include as many rollers, which, driven by a cam or in any case by a surface they encounter during the motion of the clamp around the handling wheels, determine the opening or closing of the clamp.

The number of rollers is defined so as to ensure the grip of the bottle letting it freely rotate about its own rotation axis.

Advantageously, said clamp allows the irradiation of the entire bottle without determining any screening area for the sterilizing radiations.

At the opening of the bottle and at its top, a profiled plate 204 is integral with the clamp, the plate serving the dual function of reflecting the electron beam otherwise lost on the bottle neck, and of converting the energy of the electron beam to X rays.

Said rollers 210 are adapted to hold the neck of a bottle letting it rotate about its own rotation axis.

Figure 11:
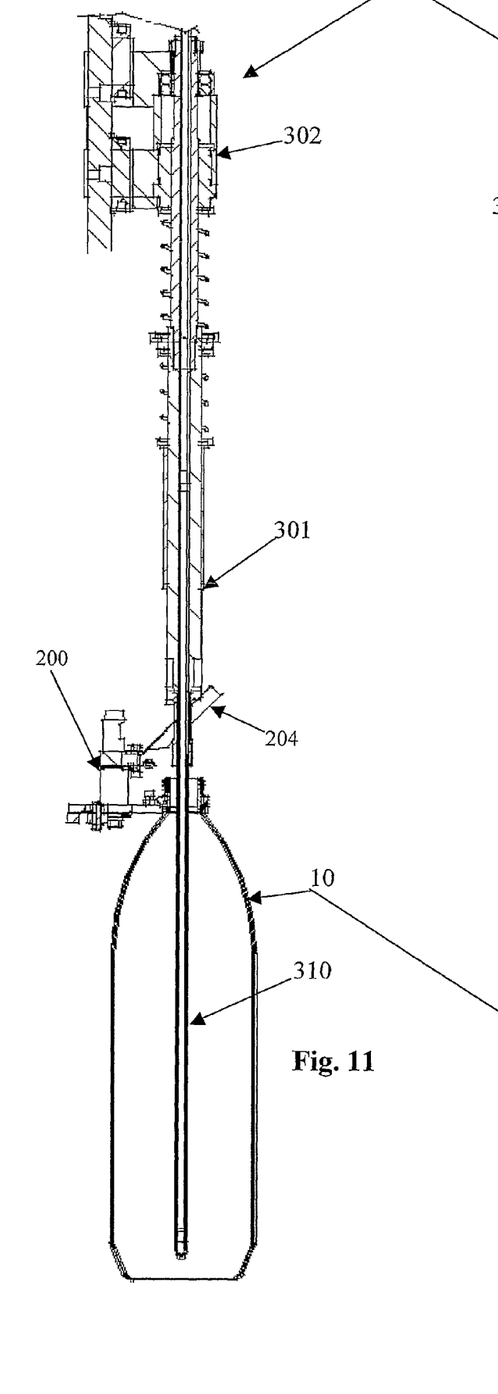
FIG. 11 shows an elaborate rotating and washing system for a container with a washing nozzle introduced in the container to be blown.
Figure 12:
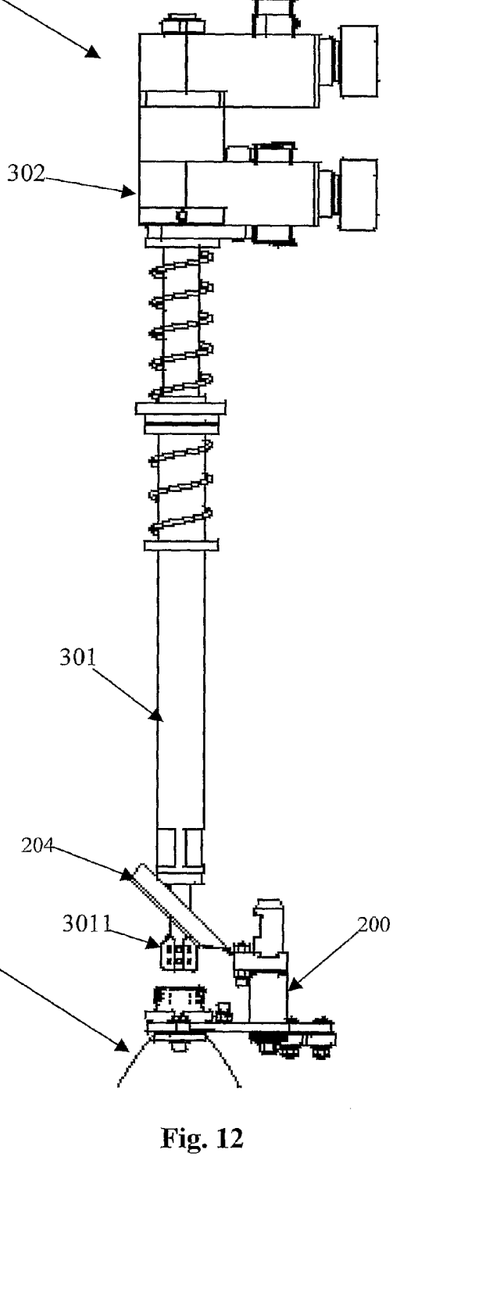
FIG. 12 shows the system before its activation.

As the rotation is required only during the irradiation of the bottle, said washing nozzle 310 is included in an elaborate system 300 which has the dual function of introducing the nozzle in the bottle and rotating the bottle.

For this purpose, said elaborate system 300 is placed in the irradiation area of the bottle.

Said elaborate system 300 includes a rotating internally hollow rod 301, including at the end 3011 a coupling compatible with the mouth of the bottle, which by being lowered to come into contact with the mouth induces the bottle to rotate.

The washing nozzle 310 is lowered through the cavity of the rotating rod 301, so that while the bottle rotates and is irradiated, it is also subjected to washing by blowing.

The rotating rod 301 is induced to rotate by means of a threading obtained along the outer surface cooperating with the support 302 of the rod, thus giving rise to a worm screw system.

At the end or during the washing, in order to achieve sterilization, said washing nozzle 310 preferredly injects in the container gaseous oxygen or a drop of liquid oxygen in an amount proportional to the size of the container, so that the electronic radiation converts it to ozone, which is highly disinfecting for the inner walls of the container.

In relation to the power of the installed generator 1, the following table shows the preferred dimensions of the screening shell 104 optimized for the power of the generator used with PET containers.

Specifically, the various areas are shown in the figures through different screens, in relation to the lower or greater degree of screening that is to be guaranteed. An A-type wall with a square screen is therefore defined in immediate proximity to the scan gun 2, a B-type screening wall with an hexagonal screen in the intermediate area and, finally, a C-type part with a 45° angled hatch near the loading and unloading area, i.e. where the radiation to be screened contains a lower energy content. The maximum and minimum cm thicknesses of each kind of wall are therefore defined in relation to the installed power in keVs of the generator 1, as shown in the following table.

| ENERGY (keV) (I max = 40 mA) | WALL "A" square hatch | | WALL "B" hexagonal hatch | | WALL "C" 45° angle hatch | |
|---|---|---|---|---|---|---|
| | Min (cm) | Max (cm) | Min (cm) | Max (cm) | Min (cm) | Max (cm) |
| 800 | 25 | 35 | 15 | 25 | 10 | 15 |
| 600 | 22 | 31 | 14 | 22 | 9 | 14 |
| 400 | 19 | 26 | 12 | 19 | 8 | 12 |
| 200 | 13 | 18 | 8 | 13 | 6 | 8 |

The invention claimed is:

1. A sterilization system for PET containers and bottles including:
   an irradiation chamber,
   an electron generator,
   a scan gun to directly irradiate said containers with an electron beam
   at least one reflector made of heavy metal adapted to deviate part of said electron beam and to convert at least one part of electron radiation to X rays to indirectly irradiate said containers, and
   deflectors for generating magnetic fields to deflect and/or focus said electron radiation on the containers during its irradiation,
   the at least one reflector being positioned in the irradiation chamber and arranged in order to convey the deviated electron beam and said X rays towards a side of the containers not directly irradiated by said electron beam.

2. A system according to claim 1, including delivery means adapted to introduce liquid or gaseous oxygen into said containers, and subject it to a direct and/or indirect radiation during the sterilization of the containers.

3. A system according to claim 1, wherein said scan gun includes a titanium window.

4. A system according to claim 1, wherein said at least one is adapted to convert to X rays a part of radiated energy in the range between 0.1% and 5%.

5. A system according to claim 1, including first handling means enclosed with said scan gun in a screening shell that screens the outer environment from the radiations the containers are subjected to during sterilization, and forming a labyrinth handling path for the containers displaying an Ω plan shape.

6. A system according to claim 5, including second handling means for capsules and caps adapted to expose the caps to direct and/indirect radiation, at least during part of the handling.

7. A system according to claim 5, including an air filtering system adapted to generate a first overpressure in introduction (IN) and ejection (OUT) areas of the containers and a second overpressure, lower than the first overpressure, in the container irradiation area.

8. A system according to claim 2, including blowing means for introducing air or inert gas or oxygen into said containers.

9. A system according to claim 8, wherein gripping means for the containers are provided, including rotating means adapted to give the containers at least a fraction of a rotation during irradiation.

10. A system according to claim 9, wherein said rotating means include a support cooperating with an internally hollow rod, including an external threading, so as to obtain a worm screw with said support, and an end including a coupling compatible with a mouth of the container to be rotated.

11. A sterilization method for PET containers and bottles including using the sterilization system of claim 1 to expose said containers to a direct electron radiation and an indirect X ray irradiation.

12. A method according to claim 11, including a previous or simultaneous step with respect to said exposure in which liquid and/or gaseous oxygen, as well as the container to be sterilized, is subjected to irradiation.

13. A method according to claim 12, wherein the electron radiation is deflected and focused on the container during the sterilization of the same.

* * * * *

UNITED STATES PATENT AND TRADEMARK OFFICE
CERTIFICATE OF CORRECTION

Page 1 of 1

PATENT NO. : 8,790,589 B2
APPLICATION NO. : 12/596003
DATED : July 29, 2014
INVENTOR(S) : Cirri et al.

It is certified that error appears in the above-identified patent and that said Letters Patent is hereby corrected as shown below:

In the Claims

Column 10, first line of Claim 4, after the word "one" insert the word -- reflector --.

Signed and Sealed this
Second Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,790,589 B2 | |
| APPLICATION NO. | : 12/596003 | |
| DATED | : July 29, 2014 | |
| INVENTOR(S) | : Cirri et al. | |

It is certified that error appears in the above-identified patent and that said Letters Patent is hereby corrected as shown below:

In the Claims

Column 10, line 10, Claim 4, after the word "one" insert the word -- reflector --.

This certificate supersedes the Certificate of Correction issued December 2, 2014.

Signed and Sealed this
Twenty-third Day of December, 2014

Michelle K. Lee
*Deputy Director of the United States Patent and Trademark Office*